(12) United States Patent
Oppenheimer et al.

(10) Patent No.: US 8,754,110 B2
(45) Date of Patent: Jun. 17, 2014

(54) METHODS OF PRODUCING METHYL 4-AMINO-3-CHLORO-6-(4-CHLORO-2-FLUORO-3-METHOXYPHENYL)PYRIDINE-2-CARBOXYLATE

(71) Applicant: Dow AgroSciences LLC, Indianapolis, IN (US)

(72) Inventors: Jossian Oppenheimer, Midland, MI (US); Mark V. M. Emonds, Midland, MI (US); Christopher W. Derstine, Midland, MI (US); Robert C. Clouse, Midland, MI (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/729,995

(22) Filed: Dec. 28, 2012

(65) Prior Publication Data

US 2013/0172566 A1 Jul. 4, 2013

Related U.S. Application Data

(60) Provisional application No. 61/582,166, filed on Dec. 30, 2011.

(51) Int. Cl.
| | | |
|---|---|---|
| *A01N 43/40* | (2006.01) | |
| *A61K 31/44* | (2006.01) | |
| *A61K 31/435* | (2006.01) | |
| *C07D 213/72* | (2006.01) | |
| *C07D 213/78* | (2006.01) | |
| *C07D 211/70* | (2006.01) | |
| *C07D 211/82* | (2006.01) | |
| *C07D 213/46* | (2006.01) | |

(52) U.S. Cl.
USPC ........... 514/352; 514/354; 514/277; 546/304; 546/310; 546/314

(58) Field of Classification Search
USPC .......................................... 546/310; 514/352
See application file for complete search history.

(56) References Cited

U.S. PATENT DOCUMENTS

| | | |
|---|---|---|
| 7,300,907 B2 | 11/2007 | Epp et al. |
| 7,314,849 B2 | 1/2008 | Balko et al. |
| 7,611,647 B2 | 11/2009 | Arndt et al. |
| 7,888,287 B2 | 2/2011 | Epp et al. |
| 2010/0311981 A1 | 12/2010 | Renga et al. |

FOREIGN PATENT DOCUMENTS

| | | |
|---|---|---|
| WO | 2006014324 A1 | 2/2006 |
| WO | 2007082098 A2 | 7/2007 |
| WO | WO2007082098 * | 7/2007 |

OTHER PUBLICATIONS

Albert J. DelMonte, Yu Fan, Kevin P. Girard, Gregory S. Jones, Robert E. Waltermire, Victor Rosso, and Xuebao Wang; Organic Process Research & Development 2011, 15, 64-72.*
Neal G. Anderson, Practical Process Research and Development, Academic Press, 2000.*
Norio Miyaura and Akira Suzuki; Chem. Rev. 1995, 95, 2457-2483.*
Kae M. Bullock, Mark B. Mitchell, and Jennifer F. Toczko; Organic Process Research & Development 2008, 12, 896-899.*
Gordon, Arnold J.; Ford, Richard A.; Chemist's Companion—A Handbook of Practical Data, Techniques, and References. (1972). John Wiley & Sons.*
Colacot, Thomas J., et al., "High-throughput screening studies of fiber-supported catalysts leading to room-temperature Suzuki coupling," Organometallics, Aug. 5, 2002, pp. 3301-3304, vol. 21, No. 16.
International Search Report and Written Opinion for PCT Application No. PCT/US2012/072071, mailed Apr. 16, 2013.

* cited by examiner

*Primary Examiner* — John Mabry
*Assistant Examiner* — Daniel Carcanague
(74) *Attorney, Agent, or Firm* — Robert Chang; TraskBritt, P.C.

(57) ABSTRACT

Methods of producing methyl 4-amino-3-chloro-6-(4-chloro-2-fluoro-3-methoxyphenyl)pyridine-2-carboxylate. One method comprises adding methyl isobutyl ketone to an aqueous solution comprising 4-chloro-2-fluoro-3-methoxyphenyl-boronic acid to form an organic phase comprising the 4-chloro-2-fluoro-3-methoxyphenylboronic acid and an aqueous phase. The organic phase and the aqueous phase are separated. The 4-chloro-2-fluoro-3-methoxyphenylboronic acid is reacted with methyl 4-(acetylamino)-3,6-dichloropyridine-2-carboxylate in methyl isobutyl ketone to produce methyl 4-(acetylamino)-3-chloro-6-(4-chloro-2-fluoro-3-methoxyphenyl)pyridine-2-carboxylate, which is deacetylated to produce methyl 4-amino-3-chloro-6-(4-chloro-2-fluoro-3-methoxyphenyl)pyridine-2-carboxylate.

19 Claims, No Drawings

METHODS OF PRODUCING METHYL 4-AMINO-3-CHLORO-6-(4-CHLORO-2-FLUORO-3-METHOXYPHENYL) PYRIDINE-2-CARBOXYLATE

CROSS-REFERENCE TO RELATED APPLICATION

This application claims the benefit of U.S. Provisional Patent Application Ser. No. 61/582,166, filed Dec. 30, 2011, the disclosure of which is hereby incorporated herein in its entirety by this reference.

TECHNICAL FIELD

Embodiments of the present disclosure relate to methods of producing methyl 4-amino-3-chloro-6-(4-chloro-2-fluoro-3-methoxyphenyl)pyridine-2-carboxylate, such as by using methyl isobutyl ketone as a solvent in multiple acts of the production of the methyl 4-amino-3-chloro-6-(4-chloro-2-fluoro-3-methoxyphenyl)pyridine-2-carboxylate.

BACKGROUND

4-Chloro-2-fluoro-3-methoxyphenylboronic acid (PBA), other 4-chloro-2-fluoro-3-substituted-phenylboronic acid derivatives, and 2-(4-chloro-2-fluoro-3-methoxyphenyl)-1,3,2-dioxaborinane (PBE) are useful intermediates in the preparation of 6-(poly-substituted aryl)-4-aminopyridine-2-carboxylate compounds and 2-(poly-substituted aryl)-6-amino-4-pyrimidinecarboxylic acid compounds, which are useful as herbicides.

PBA may be synthesized by reacting 2-chloro-6-fluoroanisole (2,6-CFA) with n-butyllithium (n-BuLi). Following subsequent reactions, the PBA is isolated as a solid. For example, the PBA is extracted from an aqueous phase using ethyl acetate and concentrated to dryness. Alternatively, the solid PBA is isolated by a crystallization process. The solid PBA is then utilized in a subsequent reaction to form the 6-(poly-substituted aryl)-4-aminopyridine-2-carboxylate compound or 2-(poly-substituted aryl)-6-amino-4-pyrimidinecarboxylic acid compound.

PBA may also be synthesized by reacting 2,6-CFA with n-BuLi and $B(OMe)_3$, adding an aqueous base to the reaction mixture, diluting the reaction mixture with acetonitrile, and acidifying the reaction mixture with hydrochloric acid. The PBA is then isolated by separating the acetonitrile and aqueous layers.

BRIEF SUMMARY

An embodiment of the present disclosure includes a method of producing methyl 4-amino-3-chloro-6-(4-chloro-2-fluoro-3-methoxyphenyl)pyridine-2-carboxylate. The method comprises adding methyl isobutyl ketone to an aqueous solution comprising 4-chloro-2-fluoro-3-methoxyphenylboronic acid to form an organic phase comprising the 4-chloro-2-fluoro-3-methoxyphenylboronic acid and an aqueous phase. The organic phase and the aqueous phase are separated. The 4-chloro-2-fluoro-3-methoxyphenylboronic acid is reacted with methyl 4-(acetylamino)-3,6-dichloropyridine-2-carboxylate in methyl isobutyl ketone to produce methyl 4-(acetylamino)-3-chloro-6-(4-chloro-2-fluoro-3-methoxyphenyl)pyridine-2-carboxylate, which is deacetylated to produce methyl 4-amino-3-chloro-6-(4-chloro-2-fluoro-3-methoxyphenyl)pyridine-2-carboxylate.

Another embodiment of the present disclosure includes a method of producing methyl 4-amino-3-chloro-6-(4-chloro-2-fluoro-3-methoxyphenyl)pyridine-2-carboxylate. The method comprises producing an aqueous solution comprising 4-chloro-2-fluoro-3-methoxyphenylboronic acid. Methyl isobutyl ketone is added to the aqueous solution. The methyl isobutyl ketone and 4-chloro-2-fluoro-3-methoxyphenylboronic acid are separated from the water. The 4-chloro-2-fluoro-3-methoxyphenylboronic acid is reacted with methyl 4-(acetylamino)-3,6-dichloropyridine-2-carboxylate in methyl isobutyl ketone to produce methyl 4-(acetylamino)-3-chloro-6-(4-chloro-2-fluoro-3-methoxyphenyl)pyridine-2-carboxylate, which is deacetylated to produce methyl 4-amino-3-chloro-6-(4-chloro-2-fluoro-3-methoxyphenyl)pyridine-2-carboxylate.

DETAILED DESCRIPTION

A method of producing methyl 4-amino-3-chloro-6-(4-chloro-2-fluoro-3-methoxyphenyl)pyridine-2-carboxylate using methyl isobutyl ketone (MIBK) as an extraction solvent, a solvent for a Suzuki coupling reaction, and/or as a solvent for a deacetylation reaction is disclosed. MIBK is also known as 4-methylpentan-2-one. The method of the present disclosure provides an increased yield of the methyl 4-amino-3-chloro-6-(4-chloro-2-fluoro-3-methoxyphenyl)pyridine-2-carboxylate compared to conventional techniques that utilize different solvents as the extraction solvent, Suzuki coupling reaction solvent, and deacetylation reaction solvent. By utilizing MIBK as the solvent for multiple process acts, solvent exchanges during the production of the methyl 4-amino-3-chloro-6-(4-chloro-2-fluoro-3-methoxyphenyl) pyridine-2-carboxylate may be minimized. Additionally, the loss of intermediate products may be reduced, increasing the yield of methyl 4-amino-3-chloro-6-(4-chloro-2-fluoro-3-methoxyphenyl)pyridine-2-carboxylate. Furthermore, the number of solvents used in the production of methyl 4-amino-3-chloro-6-(4-chloro-2-fluoro-3-methoxyphenyl)pyridine-2-carboxylate may be reduced, reducing the complexity and cost of the process.

Methyl 4-amino-3-chloro-6-(4-chloro-2-fluoro-3-methoxyphenyl)pyridine-2-carboxylate is produced from a 4-chloro-2-fluoro-3-substituted-phenylboronic acid derivative, such as PBA. As shown in the reaction scheme below, the methyl 4-amino-3-chloro-6-(4-chloro-2-fluoro-3-methoxyphenyl)pyridine-2-carboxylate (Compound 1) is produced by reacting PBA (Compound 2) with methyl 4-(acetylamino)-3,6-dichloropyridine-2-carboxylate (Compound 3) to produce methyl 4-(acetylamino)-3-chloro-6-(4-chloro-2-fluoro-3-methoxyphenyl)pyridine-2-carboxylate (Compound 4), which is deacetylated to produce Compound 1:

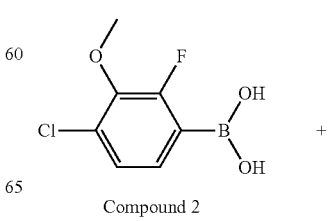

Compound 2

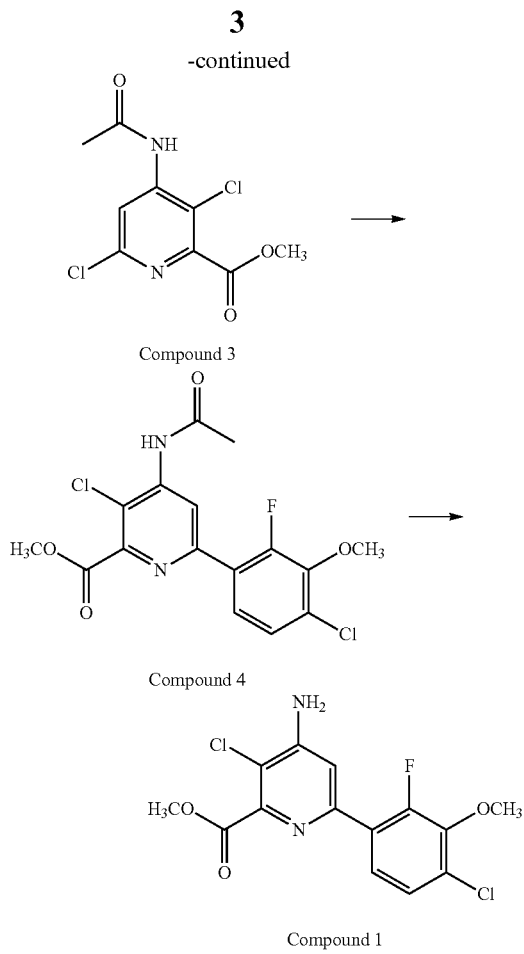

Compound 3

Compound 4

Compound 1

While embodiments of the present disclosure describe the 4-chloro-2-fluoro-3-substituted-phenylboronic acid derivative as PBA, other 4-chloro-2-fluoro-3-substituted-phenylboronic acid derivatives may also be used. For convenience, however, the 4-chloro-2-fluoro-3-substituted-phenylboronic acid derivative is described herein as PBA. MIBK may be used as the extraction solvent for producing Compound 2, the solvent for the Suzuki coupling reaction to produce Compound 4, and the solvent for the deacetylation reaction to produce Compound 1.

Provided herein is a method of recovering 4-chloro-2-fluoro-3-methoxyphenylboronic acid, comprising adding methyl isobutyl ketone to an aqueous solution comprising 4-chloro-2-fluoro-3-methoxy-phenylboronic acid to form an organic phase comprising the 4-chloro-2-fluoro-3-methoxyphenylboronic acid and an aqueous phase and separating the organic phase comprising the 4-chloro-2-fluoro-3-methoxyphenylboronic acid from the aqueous phase.

In some embodiments, the recovery is performed wherein the 4-chloro-2-fluoro-3-methoxyphenylboronic acid recovery is at least 85%. In some embodiments, the recovery is performed wherein the 4-chloro-2-fluoro-3-methoxyphenylboronic acid recovery is at least 90%.

Compound 2 may be synthesized by reacting a 1-chloro-3-fluoro-2-substituted benzene compound with an alkyl lithium compound and an electrophilic reagent in an inert organic solvent. Compound 2 is isolated from a reaction mixture that includes Compound 2, reaction by-products, and water using MIBK, which is a water-immiscible organic solvent. The reaction mixture is contacted with the MIBK to form a biphasic extraction system that includes an aqueous phase (water and any reaction by-products) and an organic phase (the MIBK and Compound 2).

Since MIBK is water-immiscible, the extraction achieves better partitioning of Compound 2 in comparison to using acetonitrile as the extraction solvent. When the organic and aqueous phases are separated, Compound 2 is obtained in solution in the organic phase (MIBK). The solution of Compound 2 may then be used directly in additional reactions, such as the reaction to form Compound 4, without conducting additional concentration or isolation acts. By eliminating recovery of Compound 2 as a solid, the yield of Compound 2 may be increased.

A reaction scheme for the preparation of a 4-chloro-2-fluoro-3-substituted-phenylboronic acid derivative from a 1-chloro-3-fluoro-2-substituted benzene starting material, an alkyl lithium compound, and an electrophilic reagent is shown below:

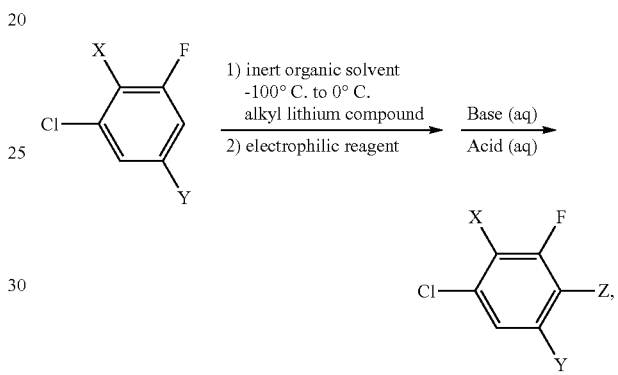

where X is F, $OR_1$, or $NR_2R_3$, Y is H or F, each of $R_1$, $R_2$, and $R_3$ is independently a methyl group, an ethyl group, a propyl group, or a butyl group, and Z is a substituent group from the electrophilic reagent. The alkyl group may be a straight chain, branched chain, or cyclic group including, but not limited to, methyl, ethyl, 1-methylethyl, propyl, cyclopropyl, butyl, 1,1-dimethylethyl, cyclobutyl, or 1-methylpropyl. The alkyl group may also be referred to as normal (n), iso (i), secondary (s), or tertiary (t) alkyl group. Z may be a bromo group, an iodo group, a sulfanyl group, a boronic acid or a boronate ester group, a sulfonyl group, a phosphoryl group, an amino group, an alkyl or acyl group, or combinations thereof. The reaction product may be contacted with an aqueous base, followed by contact with an aqueous acid, to produce the 4-chloro-2-fluoro-3-substituted-phenylboronic acid derivative. As described in detail below, MIBK may be used as the extraction solvent to isolate the 4-chloro-2-fluoro-3-substituted-phenylboronic acid derivative.

In one embodiment, Compound 2 is synthesized from 2,6-CFA by contacting the 2,6-CFA with n-BuLi and trimethyl borate (B(OMe)$_3$). A reaction scheme for the synthesis of Compound 2 from 2,6-CFA, n-BuLi, and B(OMe)$_3$ is shown below:

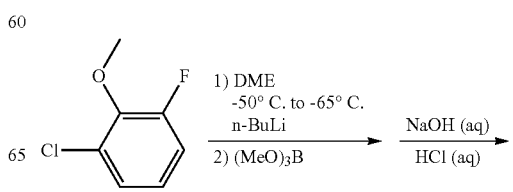

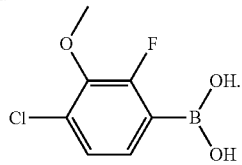

While various embodiments herein describe the synthesis of Compound 2 from 2,6-CFA, n-BuLi, and B(OMe)$_3$ and its subsequent isolation, other 4-chloro-2-fluoro-3-substituted-phenylboronic acid derivatives may be synthesized in a similar manner by utilizing appropriately selected starting materials. To synthesize Compound 2, 2,6-CFA may be contacted with the alkyl lithium compound and the electrophilic reagent in a reaction vessel. The 2,6-CFA may be produced by conventional techniques, which are not described in detail herein. The reaction may be conducted in an inert organic solvent in which the 2,6-CFA is at least partially soluble. The inert organic solvent may be a $C_5$-$C_8$ straight-chain, branched, or cyclic hydrocarbon solvent, such as a pentane, a hexane, a cyclohexane, an iso-octane, an ether, or combinations thereof. The ether may include, but is not limited to diethyl ether, tetrahydrofuran, dioxane, or a glycol ether, such as 1,2-dimethoxyethane (DME). In one embodiment, the organic solvent is DME. The 2,6-CFA may be substantially soluble in the inert organic solvent, forming a 2,6-CFA solution in which the 2,6-CFA is substantially dissolved in the inert organic solvent.

The alkyl lithium compound may include, but is not limited to methyl lithium, n-BuLi, or s-butyl lithium. In one embodiment, the alkyl lithium compound is n-BuLi. Alkyl lithium compounds are commercially available from chemical supply companies, such as Sigma-Aldrich Co. (St. Louis, Mo.). At least one molar equivalent of the alkyl lithium compound may be used relative to the 2,6-CFA. To ensure complete reaction, the alkyl lithium compound may be added in a slight excess relative to the 2,6-CFA, such as from approximately 1% to approximately 10% molar excess relative to the 2,6-CFA, or from approximately 2% to approximately 5% molar excess relative to the 2,6-CFA.

The lithiation reaction with the alkyl lithium compound may be conducted under anhydrous conditions. The lithiation reaction may be conducted at a temperature of from approximately −100° C. to approximately 0° C., such as from approximately −100° C. to approximately −50° C. The 2,6-CFA solution may be cooled to, or maintained at, a temperature within this range before addition of the alkyl lithium compound. The reaction temperature may also be maintained within this temperature range during the addition of the alkyl lithium compound. The 2,6-CFA and the alkyl lithium compound may be allowed to react for a sufficient amount of time to deprotonate the 2,6-CFA while maintaining the reaction temperature within this temperature range. The reaction may be allowed to proceed, with stirring, until the deprotonation is substantially complete. The lithiation reaction may be conducted at atmospheric pressure or greater. The reaction may be conducted under an inert atmosphere, such as by flowing nitrogen ($N_2$) or other inert gas through the reaction vessel during the reaction.

The lithiation reaction may deprotonate the carbon atom of the 1-chloro-3-fluoro-2-substituted benzene at the position (C4) between the carbon atom (C3) to which the fluoro substituent is bonded and the carbon atom (C5) to which the Y group is bonded. An intermediate compound in which lithium is bonded to the C4 carbon atom may then be formed. The lithiated 1-chloro-3-fluoro-2-substituted benzene may then be contacted with the electrophilic reagent, which reacts at the C4 position of the 1-chloro-3-fluoro-2-substituted benzene. The electrophilic reagent may function as a source of the Z group, which becomes bonded to C4 of the 1-chloro-3-fluoro-2-substituted benzene. The electrophilic reagent may be bromine, iodine, sulfur, a disulfide, sulfur dioxide, a boronic acid ester, carbon dioxide, a sulfuryl halide, a phosphoryl halide, an aldehyde, an amide, an alkyl halide, an acyl halide, or combinations thereof. The electrophilic reagent may be an alkyl borate, such as B(OMe)$_3$. In one embodiment, the electrophilic reagent is B(OMe)$_3$, which reacts with C4 of the 1-chloro-3-fluoro-2-substituted benzene to produce a boronic acid derivative. The reaction mixture including the lithiated 1-chloro-3-fluoro-2-substituted benzene may be cooled, such as from approximately −100° C. to approximately −50° C., before adding the electrophilic reagent. The electrophilic reagent may be added slowly while maintaining the temperature of the reaction mixture at or below approximately −65° C. The reaction mixture may be allowed to react for an amount of time sufficient for the electrophilic reagent to react with the lithiated 1-chloro-3-fluoro-2-substituted benzene. During the reaction with the electrophilic reagent, the temperature of the reaction mixture may be allowed to slowly increase to room temperature (from approximately 20° C. to approximately 25° C.).

An aqueous base may be added to the reaction mixture at room temperature. The aqueous base may include a base of sufficient strength to hydrolyze the reaction product of the 1-chloro-3-fluoro-2-substituted benzene and the electrophilic reagent. The base may include, but is not limited to, sodium hydroxide, potassium hydroxide, or combinations thereof. The aqueous base and the reaction mixture may be stirred for an amount of time sufficient for the base to hydrolyze the reaction product of the 1-chloro-3-fluoro-2-substituted benzene and the electrophilic reagent. The reaction mixture may then be transferred to a vessel in which the organic phase (containing hydrocarbons and some DME) and the aqueous phase (aqueous base with some dissolved DME) separate into distinct layers, which are then separated. By way of example, the vessel may be a separatory funnel. The organic phase (hydrocarbons and some DME) may be discarded, while the aqueous phase, which includes charged species of the reaction product of the 1-chloro-3-fluoro-2-substituted benzene and the electrophilic reagent, may be optionally contacted with at least one volume of an organic solvent, such as tert-butyl methyl ether (TBME), to recover unreacted 2,6-CFA. In the case where the amount of unreacted 2,6-CFA is small and not of a concern in subsequent reactions, this organic solvent wash may be omitted. In one embodiment, the aqueous phase includes a potassium salt of the reaction product of the 1-chloro-3-fluoro-2-substituted benzene and the electrophilic reagent.

The aqueous phase, which includes the charged species of the reaction product of the 1-chloro-3-fluoro-2-substituted benzene and the electrophilic reagent, may be acidified and diluted with MIBK. Since MIBK and water are not substantially miscible, distinct aqueous and organic layers may form. The aqueous phase may be acidified and then diluted with MIBK, or may be diluted with MIBK and then acidified. An aqueous acid may be added to the aqueous phase, protonating the charged species of the reaction product of the 1-chloro-3-fluoro-2-substituted benzene and the electrophilic reagent to produce Compound 2. Following the acidification, the solubility of Compound 2 in MIBK may be increased relative to the solubility of Compound 2 in acetonitrile or water. The acid may have a sufficient strength to protonate the charged species. By means of non-limiting example, the at least one acid may include hydrochloric acid (HCl). Other acids include hydrobromic acid (HBr), sulfuric acid ($H_2SO_4$), methane sulfonic acid and para-toluene sulfonic acid. The at least one acid may be used neat or may be diluted with a solvent. In at least some embodiments, the acid is 6M aqueous HCl. An equimolar amount of the acid relative to the charged species of the reaction product of the 1-chloro-3-fluoro-2-substituted benzene and the electrophilic reagent may be used. However, to ensure complete protonation, an excess of the acid may be used. By acidifying the charged species, the solubility of Compound 2 in the aqueous phase relative to its solubility in the organic phase (MIBK) may change. Once protonated, Compound 2 may be substantially insoluble in the aqueous phase but substantially soluble in MIBK. If a salt content of the MIBK/water mixture containing the acidified reaction product of the 1-chloro-3-fluoro-2-substituted benzene and the electrophilic reagent is sufficiently high, distinct aqueous and MIBK layers may form.

However, if two phases do not readily form when the MIBK is added to the aqueous phase, a salt may be added to the MIBK/water mixture. The salt may be sodium chloride, potassium chloride, calcium chloride, sodium bromide, potassium bromide, sodium sulfate, potassium sulfate, ammonium chloride, or combinations thereof. For simplicity, a metal of the salt may be the same metal as the metal of the base used in the aqueous base. By way of example, if the base was sodium hydroxide, the salt may be a sodium salt. Similarly, if the base was potassium hydroxide, the salt may be a potassium salt. The addition of the salt may occur by adding a solid form of the salt directly to the MIBK/water mixture, or by adding an aqueous salt solution to the MIBK/water mixture. The aqueous salt solution may be a saturated solution of the salt in water. By way of example, if the salt is sodium chloride, the aqueous salt solution may be a brine solution, which includes from approximately 20% by weight to approximately 27% by weight of sodium chloride in water, such as approximately 25% by weight of sodium chloride. The brine solution may also be known as a saturated sodium chloride solution. Upon addition of the salt to the MIBK/water mixture, the salt may saturate the aqueous solution, causing distinct aqueous and organic layers to form. Depending on the salt content of the MIBK/water mixture, two distinct layers may form without the addition of the salt. However, even if two distinct layers form, additional salt may be added to ensure the aqueous solution is saturated with the salt. By maximizing the saturation of the aqueous solution with the salt, recovery of the PBA from the MIBK/water mixture may be maximized. The addition of the salt may also cause Compound 2 to more readily partition into the MIBK. The MIBK and the aqueous layer may be separated, with substantially all of Compound 2 in solution in the MIBK. To recover any Compound 2 remaining in the aqueous solution, the aqueous solution may be contacted with additional volumes of MIBK. The multiple volumes of MIBK may then be combined, increasing the yield of Compound 2 obtained.

As shown in the reaction scheme below, 2,6-CFA may be lithiated with n-BuLi in anhydrous DME, forming a lithiated derivative of 2,6-CFA (Li-2,6-CFA):

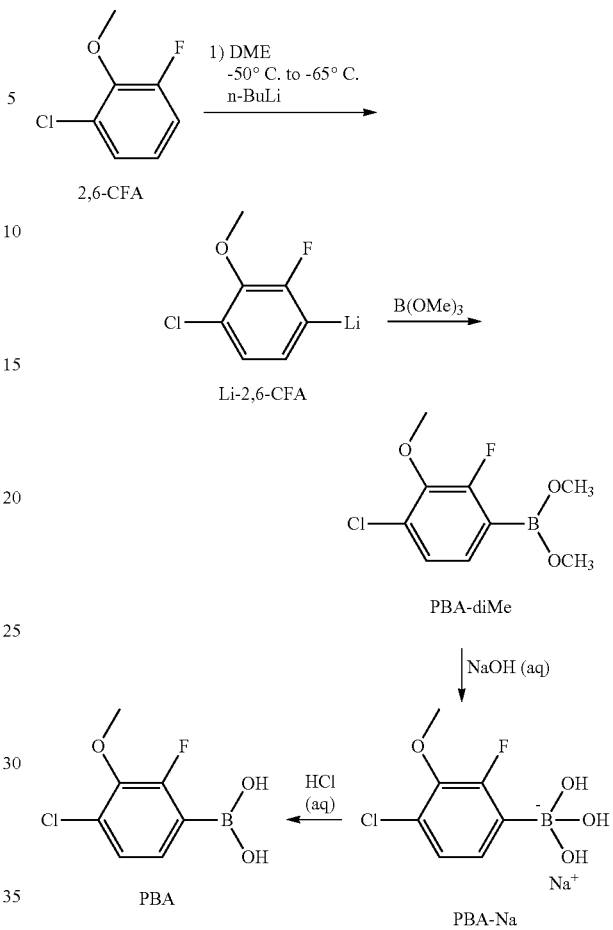

B(OMe)$_3$ may then be added and the reaction mixture slowly warmed to room temperature to faun a boronic acid derivative (PBA-di Me) of Li-2,6-CFA. A solution of sodium hydroxide in water may be added at room temperature to the PBA-di Me, forming a charged, sodium derivative (PBA-Na$^+$) of PBA-diMe. After stirring, the PBA-Na$^+$ may be transferred to a separatory funnel, where the aqueous and organic layers are allowed to separate. The aqueous layer may be washed with TBME to remove unreacted 2,6-CFA. The aqueous layer, which includes the PBA-Na$^+$, may be transferred to an Erlenmeyer flask, extracted with MIBK, and acidified by dropwise addition of 6M aqueous HCl, forming PBA (Compound 2). Alternatively, the aqueous layer including the PBA-Na$^+$ may be acidified by dropwise addition of 6 M aqueous HCl and then diluted with MIBK. While embodiments of the present disclosure describe using MIBK as the extraction solvent, MIBK may also be used in combination with other organic solvents, such as a mixture of MIBK and methanol or DME. If the MIBK is used in combination with another solvent, the MIBK may account for a majority of the total volume of the combined solvents. When other solvents are present the ratio of MIBK to DME or other solvents in the final isolated PBA solution is generally between 2:1 and 0.7:1, and more commonly between 1.6:1 and 1.2:1.

Since MIBK is not miscible with water, a saturated NaCl solution or NaCl solid may, optionally, be added to assist in formation of the aqueous and organic layers by saturating the aqueous layer with salt. Depending on the salt content of the MIBK/water mixture, two distinct layers may form without the addition of the NaCl. However, even if two distinct layers form, additional NaCl may be added to ensure the aqueous layer is saturated with NaCl. The MIBK and aqueous layers may be separated, and the aqueous layer extracted with additional volumes of MIBK. To determine the yield of Compound 2 in the MIBK, the MIBK may be removed, such as by evaporation. The white solid obtained is further dried in a vacuum oven to obtain a yield of greater than approximately 90% of Compound 2. The purity of Compound 2 may be greater than approximately 90%, such as greater than approximately 95% or greater than approximately 98%. Alternatively, Compound 2 may remain in solution in the MIBK and may be used directly in subsequent reactions without further concentration or drying, thus reducing the number of acts in the overall synthesis. Since MIBK is used as a solvent in subsequent reactions, as described below, solvent exchange may be omitted before additional acts of the methods are conducted.

Compound 2 in MIBK may be used directly in a Suzuki coupling reaction to produce Compound 4. The Suzuki coupling reaction may be conducted in MIBK alone or in combination with other organic solvents such as acetonitrile, eliminating a solvent exchange act during the production of Compound 1. Compound 2 may be reacted with methyl 4-(acetylamino)-3,6-dichloropyridine-2-carboxylate (Compound 3) in MIBK to produce Compound 4. Compound 3 (also known as 4-(acetylamino)-3,6-dichloropyridine-2-carboxylate) may be combined with triphenylphosphine and a catalyst, such as a palladium catalyst, to which is added Compound 2 in MIBK. An aqueous base, such as an aqueous potassium carbonate solution, may be added to the reaction mixture, with stirring, and the reaction allowed to proceed until the reaction is substantially complete, as monitored by gas chromatography (GC). The aqueous potassium carbonate solution may include from about 20% to about 30% potassium carbonate. The reaction mixture may be heated, such as to a temperature of from about 40° C. to about 65° C. To ensure substantially complete dissolution of the reaction products, the reaction mixture may be heated to a temperature of about 65° C. After removing reduced palladium and inorganic salts, such as by filtration, the organic and aqueous phases may be separated. The aqueous phase may be extracted with multiple volumes of MIBK to minimize product loss, the aqueous phase discarded, and the multiple volumes of MIBK combined. An aqueous sodium bisulfite solution may be added to the organic phase and the mixture heated to a temperature of from about 70° C. to about 90° C. The aqueous sodium bisulfite solution may include from about 30% to about 50% of sodium bisulfite in water, and in some embodiments, 20% to 50% of sodium bisulfite in water. After removing reduced palladium and inorganic salts, such as by filtration at a temperature of from about 65° C. to about 80° C., the organic and aqueous phases may be separated, with Compound 4 present in the organic phase. To remove additional water, which may result in product loss during the deacetylation reaction, the organic phase may be concentrated under vacuum, producing a slurry of Compound 4.

Compound 4 may be deacetylated to form Compound 1. MIBK may be used as the solvent for the deacetylation reaction. The MIBK may be used alone or in combination with another organic solvent, such as DME or excess methanol. If the MIBK is used in combination with another solvent, the MIBK may be used in certain embodiments at a ratio of from 4:6 MIBK:other solvent (v/v) to about 6:4 MIBK:other solvent. In other embodiments the ratio is about 1:2 MIBK:other solvent. To deacetylate Compound 4, methanol may be added to the slurry containing Compound 4, followed by the addition of an excess of anhydrous HCl. The slurry may be heated to a temperature of from about 40° C. to about 60° C. for an amount of time ranging from about 3 hours to about 6 hours. The reaction mixture may be monitored by GC to determine reaction completion. The reaction mixture may be cooled and an aqueous potassium carbonate solution added to the reaction mixture until a final pH of about 7.95 is reached. The aqueous potassium carbonate solution may include from about 5% potassium carbonate to about 15% potassium carbonate. The organic and aqueous phases may be separated and the organic phase transferred to a reactor vessel. A saturated sodium chloride solution may be added to the organic phase and the mixture stirred for several minutes. The resulting organic and aqueous phases may be separated and the organic phase concentrated, such as by vacuum distillation. A solvent, such as heptane or another aliphatic hydrocarbon solvent, may be added to the concentrated organic phase at a temperature of from about 65° C. to about 80° C. Addition of the solvent may cause precipitation of Compound 1. Upon completion of the heptane addition, the slurry may be cooled, such as to about 5° C. The precipitate may be collected by filtration, washed with solvent, such as additional heptane, and dried, producing Compound 1 at a yield of from about 87% to about 90% yield based on Compound 3.

By utilizing MIBK as the extraction solvent, the solvent for the Suzuki coupling reaction, and the solvent for the deacetylation reaction, the yield of Compound 1 may be greater compared to the yield obtained using conventional techniques of producing methyl 4-amino-3-chloro-6-(4-chloro-2-fluoro-3-methoxyphenyl)-pyridine-2-carboxylate. Previous methods relied on carrying out the Suzuki coupling reaction using a mixture of toluene and acetonitrile (8:1 to 10:1, toluene:acetonitrile) and tetratbutylammonium bromide (TBAB) as an additive (1 mol %) to produce compound 4 as an isolated solid at a yield from about 80% to about 90%. The crystallization process to isolate Compound 4 as a solid results in a lost in yield from about 5% to about 10% to the mother liquor. Compound 4 is redissolved in MIBK and deacetylated to give XDE729-Me in 75-82% yield based on Compound 3. By utilizing MIBK as the solvent for multiple process acts, the number of solvent exchanges during the production of Compound 1 may be minimized, which reduces the loss of intermediate products and reduces the complexity and cost of the process.

The following examples serve to explain embodiments of the present disclosure in more detail. These examples are not to be construed as being exhaustive or exclusive as to the scope of this invention.

EXAMPLES

Example 1

Synthesis and Isolation of PBA (Compound 2)

A solution of 2,6-CFA (10 g, 62.28 mmol) was lithiated using n-BuLi at a temperature below about −65° C. in anhydrous DME under a nitrogen atmosphere. B(OMe)$_3$ was added and the reaction mixture slowly warmed to room temperature. A solution of KOH in water was added to the reaction mixture at room temperature. After the addition, the temperature of the reaction mixture increased to 30° C. The reaction mixture was cooled with a cold-water bath to maintain a temperature of from approximately 25° C. to approximately 30° C. However, the reaction may be conducted without the cold-water bath, with no change in yield observed.

The reaction mixture is stirred for 90 minutes and the contents transferred to a separatory funnel where the organic and aqueous phases were allowed to separate. The bottom aqueous layer, which contained the PBA-K, was drained to a flask and acidified by the dropwise addition of 6 M aqueous HCl. Alternatively, solid KCl was added to the flask before acidification to minimize the amount of water extracted into the organic phase. The method for converting the PBA-K to PBA produced no difference in yield. After the addition, the temperature of the reaction mixture increased to 30° C. The flask was cooled with a cold-water bath to maintain a temperature of from approximately 25° C. to approximately 30° C. However, the reaction can be carried out without the cold-water bath, with no change in yield observed. The mixture was stirred for 15 minutes to achieve complete dissolution. MIBK was added, and the reaction mixture stirred for 15 minutes. The organic and aqueous phases were separated to give a solution of PBA in MIBK. Analysis of the solution gave recovery of PBA in a 90% yield.

Example 2

Synthesis and Isolation of PBA (Compound 2)

2,6-CFA (10 g, 62.28 mmol) was weighed in a separate flask and transferred to a 3-neck, 500-ml round bottom flask equipped with a thermocouple temperature probe, stir bar, and a $N_2$ inlet. The 2,6-CFA was transferred to the round bottom flask using anhydrous DME. Additional DME was added to the reaction flask to give a total DME volume of 106 ml. The reaction was cooled to −78° C. with a dry ice/acetone bath. Once the reaction reached −77° C., n-BuLi (29 ml, 71.62 mmol, 2.5 M in hexanes) was added slowly, dropwise, using a syringe pump over a 45 minute period. The highest temperature reached during addition was −70.1° C. After complete addition of n-BuLi, the reaction was left to stir for 1 hour at −74.1° C. After 1 hour, $B(OMe)_3$ (10.5 ml, 93.42 mmol) was added dropwise using a syringe pump over a period of 22 minutes. The highest temperature reached during the $B(OMe)_3$ addition was −67.0° C. After the complete addition of $B(OMe)_3$, the dry ice/acetone bath was removed and the reaction mixture warmed to room temperature (approximately 23.1° C.). Once the reaction mixture reached room temperature, the reaction was left to stir an additional 1 hour at that temperature. This procedure was repeated several times to generate a large amount of PBA-diMe in 1,2-DME. To a 1-L flask with magnetic stirrer was added 244.0 g of PBA-diMe solution (10.3% PBA basis), 27.82 g of 45% KOH, and 108.70 g of deionized $H_2O$. The flask was cooled with a cold-water bath to maintain a temperature of 25° C.-30° C. during the addition. However, the reaction can be conducted without the cold-water bath, with no change in yield observed. The mixture was stirred for about 2 hours and vacuum filtered to remove lithium salts. The organic and aqueous phases were separated. To the aqueous phase was added 4.51 g of KCl and then 40.48 g of concentrated HCl. In an alternative procedure, solid KCl was added to the aqueous phase before acidification to minimize the amount of water extracted into the organic phase, with no change in yield observed. The solution was cooled with a cold-water bath during the addition to maintain a temperature of 25° C.-30° C. during the addition. However, the reaction can be conducted without the cold-water bath, with no change in yield observed. The mixture was stirred for 15 minutes to achieve complete dissolution. MIBK (35.91 g) was added and the solution stirred for about 15 minutes. The organic and aqueous phases were separated to give 127.6 g of the organic phase. Analysis of the solution gave 17.57% by weight of PBA, for a PBA recovery of 89.1%.

Example 3

Synthesis of methyl 4-(acetylamino)-3-chloro-6-(4-chloro-2-fluoro-3-methoxyphenyl)pyridine-2-carboxylate (Compound 4)

To a 1 L jacketed vessel equipped with condenser, thermocouple temperature probe, mechanical stirrer and $N_2$ inlet was added methyl 4-(acetylamino)-3,6-dichloropyridine-2-carboxylate (AcAP-Me, 40 g, 152 mmol). To the vessel is added triphenylphosphine ($PPh_3$, 598 mg, 2.28 mmol) followed by tetrabutylammonium bromide (TBAB, 368 mg, 1.14 mmol). The solids are dissolved in toluene (224 mL) and sparged with nitrogen for 30 min with stirring (180 rpm). After sparging for 30 min, 1,3-propanediyl-4-chloro-2-fluoro-3-methoxyphenylboronate (PBE, 46.5 g, 190 mmol) is added. In a separate flask palladium(II) acetate [$Pd(OAc)_2$, 256 mg, 1.14 mmol] is added and dissolved in acetonitrile (previously sparged for 30 min with nitrogen, 28 mL). The solution of the palladium(II) acetate in acetonitrile is then added to the reaction mixture and the agitation is increased to 300 RPM. The reaction mixture is stirred for 5 min before adding an aqueous solution of $K_2CO_3$ (22.8%, 228 mL, previously sparged for 30 min with nitrogen). The reaction mixture is heated to 65° C. and stirred for 2 h. After 2 h, the reaction is sampled by GC to determine completion of the reaction. Once the reaction is complete the agitation is stopped and the phases are left to settle. The aqueous layer is drained hot (~60° C.) into a flask. The organic phase is sampled by GC using an internal standard (valerophenone) to determine an in-pot yield. The GC analysis showed an in-pot yield of 53.98 g, 95% of Ac729-Me. The organic phase is then washed at 65° C. with an aqueous saturated solution of NaCl (26%, 150 mL) After 30 min the agitation is stopped and layers are left to settle. The aqueous layer is drained hot (60° C.) into a beaker. The circulator bath is then set to 40.0° C. and the reaction mixture is left to cool slowly to 40° C. When the reaction temperature reached 45° C., the solution became cloudy and eventually a lot of solid product crystallized out at 40° C. Isopar C (265 mL) is then added slowly using an addition funnel at 40° C. The lowest temperature reached during the addition of isopar C is 37.6° C. The circulator bath is then set to 24.0° C. and the reaction mixture left to cool overnight. The next morning the product is recovered by filtration using Buchner funnel and #1 filter paper. The filter cake is then washed with a 1:1 mixture of toluene:isopar C (100 mL). The solid is further dried in a vacuum oven at 55° C. overnight to give Ac729-Me as a light brown solid (45.6 g, 81%). Total yield (isolated yield+product in filtrate)=52.8 g, 93% yield of Ac729-Me.

Example 4

Synthesis of methyl 4-amino-3-chloro-6-(4-chloro-2-fluoro-3-methoxyphenyl)pyridine-2-carboxylate (Compound 1)

Methyl 4-(acetylamino)-3-chloro-6-(4-chloro-2-fluoro-3-methoxyphenyl)pyridine-2-carboxylate (Compound 4) (9.0352 g) was loaded into a 100 mL three-necked flask equipped with a magnetic stirrer, heating mantle, thermometer, and condenser under a nitrogen atmosphere. Methanol (8.1 mL) was added, followed by 4-methyl-2-pentanone (MIBK, 26 mL). The resulting slurry was mixed, and anhydrous hydrogen chloride was introduced by adding 1.2 mL of acetyl chloride via syringe over 6 min. The acetyl chloride reacts with the methanol to form one equivalent of anhydrous hydrogen chloride and one equivalent of methyl acetate. Upon completion of the acetyl chloride addition, the mixture was heated to 50° C. and stirred at that temperature for seven hours. The remaining solid compound 4 initially dissolved to give a clear solution, which again formed a slurry over time. The resulting mixture was then cooled to ambient temperature and treated with saturated aqueous sodium hydrogen carbonate solution (20 mL). The solids dissolved and gas evolution ($CO_2$) was evident. The mixture was transferred to a separatory funnel and separated. The organic phase was washed with saturated aqueous sodium chloride (20.5 mL). The resulting organic phase was then transferred to a 100 mL three-necked flask equipped with a magnetic stir bar, thermometer, heating mantle, and distillation head. The system was placed under vacuum (115 mmHg) and was heated to distill out a portion of the solvent. Approximately 15.5 mL of solvent was taken overhead, and additional MIBK (4.8 mL) was added to the distillation bottoms and the mixture was warmed to 55° C. Heptane (50 mL) was added dropwise to the clear solution over 20 min, resulting in the precipitation of the product. The product was recovered by filtration through Whatman #50 paper using a Buchner funnel. The filter cake was washed with heptane (20 mL), then dried overnight under vacuum. A total of 4.3506 g of methyl 4-amino-3-chloro-6-(4-chloro-2-fluoro-3-methoxyphenyl)pyridine-2-carboxylate was obtained (91.9% pure by HPLC assay, 92.6% yield based on loaded compound 4).

Example 5

Synthesis of methyl 4-(acetylamino)-3-chloro-6-(4-chloro-2-fluoro-3-methoxyphenyl)pyridine-2-carboxylate (Compound 4)

To a 1-L jacketed reactor equipped with a condenser, mechanical stirrer, thermocouple temperature probe, and nitrogen inlet was added 40.0 g of methyl 4-(acetylamino)-3,6-dichloropyridine-2-carboxylate (AcAP-Me), 0.4 g of triphenylphosphine, and 0.17 g of palladium(II) acetate under a nitrogen atmosphere. A 25 ml rinse with acetonitrile (previously degassed by sparging with nitrogen for 45 minutes) was employed to ensure all solids were transferred to the reactor. A total of 157.1 g of a 22% solution of PBA (prepared as described in Example 1 or Example 2 and previously degassed by sparging with nitrogen for 45 minutes) in 1,2-dimethoxyethane (DME) and methyl isobutyl ketone (MIBK) was added under nitrogen via a pump. The ratio of MIBK to DME in the PBA solution varies from 2:1 to 0.7:1 (MIBK:DME) depending on the equivalents of the solvents used to prepare the PBA solution, or more commonly from 1.6:1 to 1.2:1. Stirring at 300 RPM was initiated. An additional 100 ml of acetonitrile (previously degassed by sparging with nitrogen for 45 minutes) was added and complete dissolution was achieved. A total of 275.3 g of a 22.9% aqueous solution of potassium carbonate (previously degassed by sparging with nitrogen for 45 minutes) was added via a pump. The solution was heated to about 50° C. for 2.5 hours. Towards the end of the reaction, the product tended to precipitate and a small product rind formed on the reactor wall. The organic phase of the mixture was sampled and analyzed by GC to determine reaction completion.

The mixture was heated to about 65° C. to ensure complete product dissolution. The mixture was filtered (polish filtration) at 65° C. to remove reduced palladium and inorganic salts. The organic and aqueous phases were separated at 65° C. and the organic (top) phase was transferred to a 1-L reactor equipped with a mechanical stirrer, condenser, thermocouple temperature probe, and nitrogen inlet. A total of 71.7 g of MIBK was added as a rinse to facilitate the transfer. A total of 380 ml of a 40% sodium bisulfite solution was added and the mixture was heated to about 80° C. for about 6 hours. The mixture was filtered at 80° C. to remove reduced palladium and inorganic salts and the phases were separated. The phase separation can be conducted at a temperature as low as 65° C. The organic phase (top) was transferred to a 1-L reactor equipped with a mechanical stirrer, distillation head, temperature probe, and vacuum capability. The mixture was concentrated under vacuum in order to remove water from the mixture, resulting in a slurry of methyl 4-(acetylamino)-3-chloro-6-(4-chloro-2-fluoro-3-methoxyphenyl)pyridine-2-carboxylate.

Example 6

Synthesis of methyl 4-amino-3-chloro-6-(4-chloro-2-fluoro-3-methoxyphenyl)pyridine-2-carboxylate (Compound 1)

To the slurry of methyl 4-(acetylamino)-3-chloro-6-(4-chloro-2-fluoro-3-methoxyphenyl)pyridine-2-carboxylate (prepared as described in Example 5) was added 144 ml of methanol at 25° C. To this slurry was sparged 6.0 g (1.3 equivalents) of anhydrous HCl and the slurry was heated to 50° C. for between 4 hours and 5 hours. The solution was sampled and analyzed by GC to determine reaction completion. The reaction time is dependent on the equivalents of anhydrous HCl employed in the reaction. Using larger excesses of HCl, such as above 1.3 equivalents of HCl, results in shorter reaction times. However, increased volumes of base are subsequently required in the neutralization/work-up to neutralize the excess acid. The reaction mixture was cooled to 25° C. and 127.1 g of a 10% potassium carbonate solution was slowly added until a pH of 7.95 was reached. The organic and aqueous phases were separated and the organic (top) phase was transferred to a 1-L reactor. A total of 140 ml of a saturated sodium chloride solution was added and the mixture was stirred for several minutes. The organic and aqueous phases were separated and the organic (top) phase was transferred to a 1-L reactor equipped with a mechanical stirrer, distillation head, temperature probe, and vacuum capability. The organic phase was concentrated via a vacuum distillation to about a 30% by weight solution. To the solution at 70° C. was added 662.8 g of heptane over 45 minutes. After adding about half of the heptane; a product began to precipitate from solution. The minimum temperature during the heptane addition was 65° C. Upon completion of the heptane addition, the slurry was cooled to about 5° C. The product was collected by filtration and washed with 195 ml of heptane. The product was dried in a vacuum oven at 55° C. overnight to give 87%-90% yield (based on AcAP-Me) of methyl 4-amino-3-chloro-6-(4-chloro-2-fluoro-3-methoxyphenyl)pyridine-2-carboxylate.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

What is claimed is:

1. A method of producing methyl 4-amino-3-chloro-6-(4-chloro-2-fluoro-3-methoxyphenyl)pyridine-2-carboxylate, comprising:
adding methyl isobutyl ketone to an aqueous solution comprising 4-chloro-2-fluoro-3-methoxyphenylboronic acid to form a methyl isobutyl ketone solution comprising the 4-chloro-2-fluoro-3-methoxyphenylboronic acid and an aqueous phase;
separating the methyl isobutyl ketone solution comprising the 4-chloro-2-fluoro-3-methoxyphenylboronic acid from the aqueous phase;
reacting the 4-chloro-2-fluoro-3-methoxyphenylboronic acid in the methyl isobutyl ketone solution with methyl 4-(acetylamino)-3,6-dichloropyridine-2-carboxylate, without concentrating or isolating the 4-chloro-2-fluoro-3-methoxyphenylboronic acid from the methyl isobutyl ketone solution, to produce methyl 4-(acetylamino)-3-chloro-6-(4-chloro-2-fluoro-3-methoxyphenyl)pyridine-2-carboxylate; and
deacetylating the methyl 4-(acetylamino)-3-chloro-6-(4-chloro-2-fluoro-3-methoxyphenyl)pyridine-2-carboxylate to produce methyl 4-amino-3-chloro-6-(4-chloro-2-fluoro-3-methoxyphenyl)pyridine-2-carboxylate.

2. The method of claim 1, wherein adding methyl isobutyl ketone to an aqueous solution comprising 4-chloro-2-fluoro-3-methoxyphenylboronic acid comprises partitioning the 4-chloro-2-fluoro-3-methoxyphenylboronic acid into the methyl isobutyl ketone.

3. The method of claim 1, wherein reacting the 4-chloro-2-fluoro-3-methoxyphenylboronic acid in the methyl isobutyl ketone solution with methyl 4-(acetylamino)-3,6-dichloropyridine-2-carboxylate comprises reacting the 4-chloro-2-fluoro-3-methoxyphenylboronic acid, the methyl 4-(acetylamino)-3,6-dichloropyridine-2-carboxylate, triphenylphosphine, and a palladium catalyst in the methyl isobutyl ketone solution.

4. The method of claim 1, wherein deacetylating the methyl 4-(acetylamino)-3-chloro-6-(4-chloro-2-fluoro-3-methoxyphenyl)pyridine-2-carboxylate comprises deacetylating the methyl 4-(acetylamino)-3-chloro-6-(4-chloro-2-fluoro-3-methoxyphenyl)pyridine-2-carboxylate in methyl isobutyl ketone.

5. The method of claim 1, wherein deacetylating the methyl 4-(acetylamino)-3-chloro-6-(4-chloro-2-fluoro-3-methoxyphenyl)pyridine-2-carboxylate comprises reacting the methyl 4-(acetylamino)-3-chloro-6-(4-chloro-2-fluoro-3-methoxyphenyl)pyridine-2-carboxylate with anhydrous hydrochloric acid.

6. The method of claim 1, further comprising adding a salt to a mixture of the methyl isobutyl ketone solution comprising the 4-chloro-2-fluoro-3-methoxyphenylboronic acid and the aqueous phase.

7. The method of claim 6, wherein adding a salt to a mixture of the methyl isobutyl ketone solution comprising the 4-chloro-2-fluoro-3-methoxyphenylboronic acid and the aqueous phase comprises adding a saturated solution of sodium chloride to the mixture.

8. A method of producing methyl 4-amino-3-chloro-6-(4-chloro-2-fluoro-3-methoxyphenyl)pyridine-2-carboxylate, comprising:
producing an aqueous solution comprising 4-chloro-2-fluoro-3-methoxyphenylboronic acid;
adding methyl isobutyl ketone to the aqueous solution comprising the 4-chloro-2-fluoro-3-methoxyphenylboronic acid to form a methyl isobutyl ketone solution comprising the 4-chloro-2-fluoro-3-methoxyphenylboronic acid and an aqueous phase;
separating the methyl isobutyl ketone solution comprising the 4-chloro-2-fluoro-3-methoxyphenylboronic acid from the aqueous phase;
reacting the 4-chloro-2-fluoro-3-methoxyphenylboronic acid in the methyl isobutyl ketone solution with methyl 4-(acetylamino)-3,6-dichloropyridine-2-carboxylate, without concentrating or isolating the 4-chloro-2-fluoro-3-methoxyphenylboronic acid from the methyl isobutyl ketone solution, to produce methyl 4-(acetylamino)-3-chloro-6-(4-chloro-2-fluoro-3-methoxyphenyl)pyridine-2-carboxylate; and
deacetylating the methyl 4-(acetylamino)-3-chloro-6-(4-chloro-2-fluoro-3-methoxyphenyl)pyridine-2-carboxylate to produce methyl 4-amino-3-chloro-6-(4-chloro-2-fluoro-3-methoxyphenyl)pyridine-2-carboxylate.

9. The method of claim 8, wherein producing an aqueous solution comprising 4-chloro-2-fluoro-3-methoxyphenylboronic acid comprises:
contacting 2-chloro-6-fluoroanisole (2,6-CFA) with n-butyl lithium to produce a lithiated derivative of 2,6-CFA;
contacting the lithiated derivative of 2,6-CFA with trimethyl borate to produce a boronic acid derivative of 2,6-CFA;
contacting the boronic acid derivative of 2,6-CFA with aqueous sodium hydroxide to produce a sodium salt of the boronic acid derivative of 2,6-CFA; and
contacting the sodium salt of the boronic acid derivative of 2,6-CFA with aqueous hydrochloric acid.

10. The method of claim 8, wherein reacting the 4-chloro-2-fluoro-3-methoxyphenylboronic acid in methyl isobutyl ketone solution with methyl 4-(acetylamino)-3,6-dichloropyridine-2-carboxylate to produce methyl 4-(acetylamino)-3-chloro-6-(4-chloro-2-fluoro-3-methoxyphenyl)pyridine-2-carboxylate comprises:
adding an aqueous base to a reaction product of the 4-chloro-2-fluoro-3-methoxyphenylboronic acid and methyl 4-(acetylamino)-3,6-dichloropyridine-2-carboxylate to produce a first aqueous phase and a first organic phase;
separating the first aqueous phase and the first organic phase;
adding an aqueous sodium bisulfite solution to the first organic phase to produce a second aqueous phase and a second organic phase;
separating the second aqueous phase and the second organic phase; and
concentrating the second organic phase in vacuo.

11. The method of claim 8, wherein producing an aqueous solution comprising 4-chloro-2-fluoro-3-methoxyphenylboronic acid comprises:
contacting 2-chloro-6-fluoroanisole (2,6-CFA) with n-butyl lithium to produce a lithiated derivative of 2,6-CFA;
contacting the lithiated derivative of 2,6-CFA with trimethyl borate to produce a boronic acid derivative of 2,6-CFA;
contacting the boronic acid derivative of 2,6-CFA with aqueous potassium hydroxide to produce a potassium salt of the boronic acid derivative of 2,6-CFA; and
contacting the potassium salt of the boronic acid derivative of 2,6-CFA with aqueous hydrochloric acid.

12. The method of claim 8, wherein deacetylating the methyl 4-(acetylamino)-3-chloro-6-(4-chloro-2-fluoro-3-methoxyphenyl)pyridine-2-carboxylate comprises adding methanol and anhydrous hydrochloric acid to the methyl 4-(acetylamino)-3-chloro-6-(4-chloro-2-fluoro-3-methoxyphenyl)pyridine-2-carboxylate.

13. The method of claim 8, wherein deacetylating the methyl 4-(acetylamino)-3-chloro-6-(4-chloro-2-fluoro-3-methoxyphenyl)pyridine-2-carboxylate to produce methyl 4-amino-3-chloro-6-(4-chloro-2-fluoro-3-methoxyphenyl)pyridine-2-carboxylate comprises forming the methyl 4-amino-3-chloro-6-(4-chloro-2-fluoro-3-methoxyphenyl)pyridine-2-carboxylate at a yield of from about 87% to about 90% based on methyl 4-(acetylamino)-3,6-dichloropyridine-2-carboxylate.

14. A method of producing methyl 4-amino-3-chloro-6-(4-chloro-2-fluoro-3-methoxyphenyl)pyridine-2-carboxylate, comprising:
    contacting 2-chloro-6-fluoroanisole (2,6-CFA) with n-butyl lithium to produce a lithiated derivative of 2,6-CFA;
    contacting the lithiated derivative of 2,6-CFA with trimethyl borate to produce a boronic acid derivative of 2,6-CFA;
    contacting the boronic acid derivative of 2,6-CFA with aqueous sodium hydroxide to produce an aqueous phase comprising a sodium salt of the boronic acid derivative of 2,6-CFA;
    contacting the aqueous phase comprising the sodium salt of the boronic acid derivative of 2,6-CFA with aqueous hydrochloric acid to produce an aqueous solution comprising 4-chloro-2-fluoro-3-methoxyphenylboronic acid;
    adding methyl isobutyl ketone to the aqueous solution to form a methyl isobutyl ketone solution comprising the 4-chloro-2-fluoro-3-methoxyphenylboronic acid;
    separating the methyl isobutyl ketone solution comprising the 4-chloro-2-fluoro-3-methoxy phenylboronic acid from the water;
    reacting methyl 4-(acetylamino)-3,6-dichloropyridine-2-carboxylate with the 4-chloro-2-fluoro-3-methoxyphenylboronic acid in the methyl isobutyl ketone solution, without concentrating or isolating the 4-chloro-2-fluoro-3-methoxyphenylboronic acid from the methyl isobutyl ketone solution, in the presence of a palladium catalyst, a phosphine ligand, and an aqueous base to produce methyl 4-(acetylamino)-3-chloro-6-(4-chloro-2-fluoro-3-methoxyphenyl)pyridine-2-carboxylate; and
    deacetylating the methyl 4-(acetylamino)-3-chloro-6-(4-chloro-2-fluoro-3-methoxyphenyl)pyridine-2-carboxylate in the methyl isobutyl ketone to produce methyl 4-amino-3-chloro-6-(4-chloro-2-fluoro-3-methoxyphenyl)pyridine-2-carboxylate.

15. The method of claim 14, wherein deacetylating the methyl 4-(acetylamino)-3-chloro-6-(4-chloro-2-fluoro-3-methoxyphenyl)pyridine-2-carboxylate comprises adding methyl isobutyl ketone, methanol, and anhydrous hydrochloric acid to the methyl 4-(acetylamino)-3-chloro-6-(4-chloro-2-fluoro-3-methoxyphenyl)pyridine-2-carboxylate.

16. The method of claim 14, wherein deacetylating the methyl 4-(acetylamino)-3-chloro-6-(4-chloro-2-fluoro-3-methoxyphenyl)pyridine-2-carboxylate to produce methyl 4-amino-3-chloro-6-(4-chloro-2-fluoro-3-methoxyphenyl)pyridine-2-carboxylate comprises forming the methyl 4-amino-3-chloro-6-(4-chloro-2-fluoro-3-methoxyphenyl)pyridine-2-carboxylate at a yield of from about 87% to about 90% based on methyl 4-(acetylamino)-3,6-dichloropyridine-2-carboxylate.

17. A method of producing methyl 4-amino-3-chloro-6-(4-chloro-2-fluoro-3-methoxyphenyl)pyridine-2-carboxylate, comprising:
    contacting 2-chloro-6-fluoroanisole (2,6-CFA) with n-butyl lithium to produce a lithiated derivative of 2,6-CFA;
    contacting the lithiated derivative of 2,6-CFA with trimethyl borate to produce a boronic acid derivative of 2,6-CFA;
    contacting the boronic acid derivative of 2,6-CFA with aqueous potassium hydroxide to produce an aqueous phase comprising a potassium salt of the boronic acid derivative of 2,6-CFA;
    contacting the aqueous phase comprising the potassium salt of the boronic acid derivative of 2,6-CFA with aqueous hydrochloric acid to produce an aqueous solution comprising 4-chloro-2-fluoro-3-methoxyphenylboronic acid;
    adding methyl isobutyl ketone to the aqueous solution to form a methyl isobutyl ketone solution comprising the 4-chloro-2-fluoro-3-methoxyphenylboronic acid;
    separating the methyl isobutyl ketone solution comprising the 4-chloro-2-fluoro-3-methoxy phenylboronic acid from the water;
    reacting methyl 4-(acetylamino)-3,6-dichloropyridine-2-carboxylate with the 4-chloro-2-fluoro-3-methoxyphenylboronic acid in the methyl isobutyl ketone solution, without concentrating or isolating the 4-chloro-2-fluoro-3-methoxyphenylboronic acid from the methyl isobutyl ketone solution, in the presence of a palladium catalyst, a phosphine ligand, and an aqueous base to produce methyl 4-(acetylamino)-3-chloro-6-(4-chloro-2-fluoro-3-methoxyphenyl)pyridine-2-carboxylate; and
    deacetylating the methyl 4-(acetylamino)-3-chloro-6-(4-chloro-2-fluoro-3-methoxyphenyl)pyridine-2-carboxylate in the methyl isobutyl ketone to produce methyl 4-amino-3-chloro-6-(4-chloro-2-fluoro-3-methoxyphenyl)pyridine-2-carboxylate.

18. The method of claim 17, wherein deacetylating the methyl 4-(acetylamino)-3-chloro-6-(4-chloro-2-fluoro-3-methoxyphenyl)pyridine-2-carboxylate comprises adding methyl isobutyl ketone, methanol, and anhydrous hydrochloric acid to the methyl 4-(acetylamino)-3-chloro-6-(4-chloro-2-fluoro-3-methoxyphenyl)pyridine-2-carboxylate.

19. The method of claim 17, wherein deacetylating the methyl 4-(acetylamino)-3-chloro-6-(4-chloro-2-fluoro-3-methoxyphenyl)pyridine-2-carboxylate to produce methyl 4-amino-3-chloro-6-(4-chloro-2-fluoro-3-methoxyphenyl)pyridine-2-carboxylate comprises forming the methyl 4-amino-3-chloro-6-(4-chloro-2-fluoro-3-methoxyphenyl)pyridine-2-carboxylate at a yield of from about 87% to about 90% based on methyl 4-(acetylamino)-3,6-dichloropyridine-2-carboxylate.

* * * * *